United States Patent [19]

Schulman et al.

[11] 4,220,156
[45] Sep. 2, 1980

[54] LOW POWER IMPLANTABLE APPARATUS AND METHOD FOR RECEIVING AN AM SIGNAL

[75] Inventors: Joseph H. Schulman, Los Angeles; Wayne A. Morgan, Granada Hills, both of Calif.

[73] Assignee: Pacesetter Systems, Inc., Sylmar, Calif.

[21] Appl. No.: 957,440

[22] Filed: Nov. 3, 1978

[51] Int. Cl.³ .............................................. A61N 1/00
[52] U.S. Cl. ................................. 128/419 R; 128/903
[58] Field of Search .............. 128/696, 901, 902, 903, 128/904, 702, 708, 419 PG, 419 PT, 419 C, 419 E, 419 R

[56] References Cited

U.S. PATENT DOCUMENTS

| | | | |
|---|---|---|---|
| 3,498,288 | 3/1970 | Max et al. | 128/696 |
| 3,520,295 | 7/1970 | Kelly | 128/708 |
| 3,796,221 | 3/1974 | Hagfors | 128/419 C |
| 3,833,005 | 9/1974 | Wingrove | 128/419 PG |
| 3,939,824 | 2/1976 | Arneson et al. | 128/901 |

Primary Examiner—William E. Kamm
Attorney, Agent, or Firm—Frelich, Hornbaker, Wasserman, Rosen & Fernandez

[57] ABSTRACT

An implantable AM receiver having a variable threshold which can detect signals above a changing noise level. An AM receiver is provided which provides a modulation envelope corresponding to the amplitude of a pulse-modulated RF signal radiated by an external device. A voltage signal is developed which is at least equal to the amplitude of the modulation envelope, but which decays at a predetermined rate if the modulation envelope drops to a value below the voltage signal. The voltage signal is then scaled to a predetermined percentage of a value corresponding to the value of the modulation envelope, and biased so that it cannot drop below a predetermined minimum level. The scaled voltage signal comprises the variable threshold and is compared by a comparator to the modulation envelope. If it is below the modulation envelope, the comparator outputs a voltage having a first state; if it is above the modulation envelope, the comparator outputs a voltage having a second state.

11 Claims, 3 Drawing Figures

LOW POWER IMPLANTABLE APPARATUS AND METHOD FOR RECEIVING AN AM SIGNAL

BACKGROUND OF THE INVENTION

1. Field of the Invention

The present invention generally relates to implanted devices and more particularly to an implantable low power receiver for implementation in a living body to receive signals transmitted thereto from an external source.

2. Description of the Prior Art

In the field of medical instrumentation, a significant effort is being directed to develop instruments which are implantable in a living body to perform or monitor various functions. One such device which is most widely known by the public at large is the cardiac pacemaker, or simply the heart pacer. Many advances have been made in the field of implantable instrumentation, particularly in recent years. Devices have been proposed to stimulate organs other than the heart, e.g., the brain and spine. Some of these devices include one or more implantable receivers. The function of the implanted receiver is to receive modulated signals from a source, external to the body, and then supply demodulated signals to various circuits to control their operations. One such arrangement is developed in U.S. Pat. No. 3,918,461, wherein implanted receivers are used to receive signals from an external transmitter and supply signals to brain-stimulating electrodes.

For proper operation of the receiver, it is important that it be insensitive to noise when the received signal is greater than the noise. FM receivers are very sensitive, since their noise rejection is higher. However, a conventional FM receiver requires a separate power source, e.g., a battery. In any implantable device the amount of power which is available from the power source is limited. The need to power an FM receiver, which has to be powered continuously, would result in an appreciable power drainage. Thus, the use of a conventional FM receiver in an implantable device is undesirable from the power consumption point of view.

An FM receiver, such as a crystal set, is one which can be powered by the signal carrier energy. However, in order to be sensitive, the AM receiver needs a low threshold. Yet, with a low threshold, a danger exists that the receiver will become jammed by ever-present unwanted noise. Thus, whereas the use of an FM receiver in an implanted device is undesirable from a power consumption point of view, a conventional AM receiver cannot be used because of its possible jamming by noise.

OBJECTS AND SUMMARY OF THE INVENTION

It is an objective of the present invention to provide a new implantable AM receiver.

Another objective of the present invention is to provide an improved AM receiver for use in an implantable device which is capable of distinguishing between received signals and noise.

A further objective of the present invention is to provide a new improved AM receiver of the implantable type, which is operable in the presence of noise which may be of varying amplitude, and which can detect signals above the noise level.

A still further objective of the invention is to provide an improved method for receiving a pulse amplitude modulated RF signal by an implanted AM receiver in the presence of noise which may be of varying amplitude.

These and other objectives of the invention are achieved by providing an AM type receiver having a variable threshold, which varies automatically as a function of the amplitudes of received signals and/or noise. In the absence of noise the receiver is sensitive to very small-amplitude signals. On the other hand, in the presence of noise the receiver becomes less sensitive so that if the amplitude of the signals transmitted to the receiver is increased, the signals will be detected even in the presence of noise.

The novel features of the invention are set forth with particularity in the appended claims. The invention will best be understood from the following description when read in conjunction with the accompanying drawings.

DESCRIPTION OF THE PREFERRED EMBODIMENTS

Figure 1:
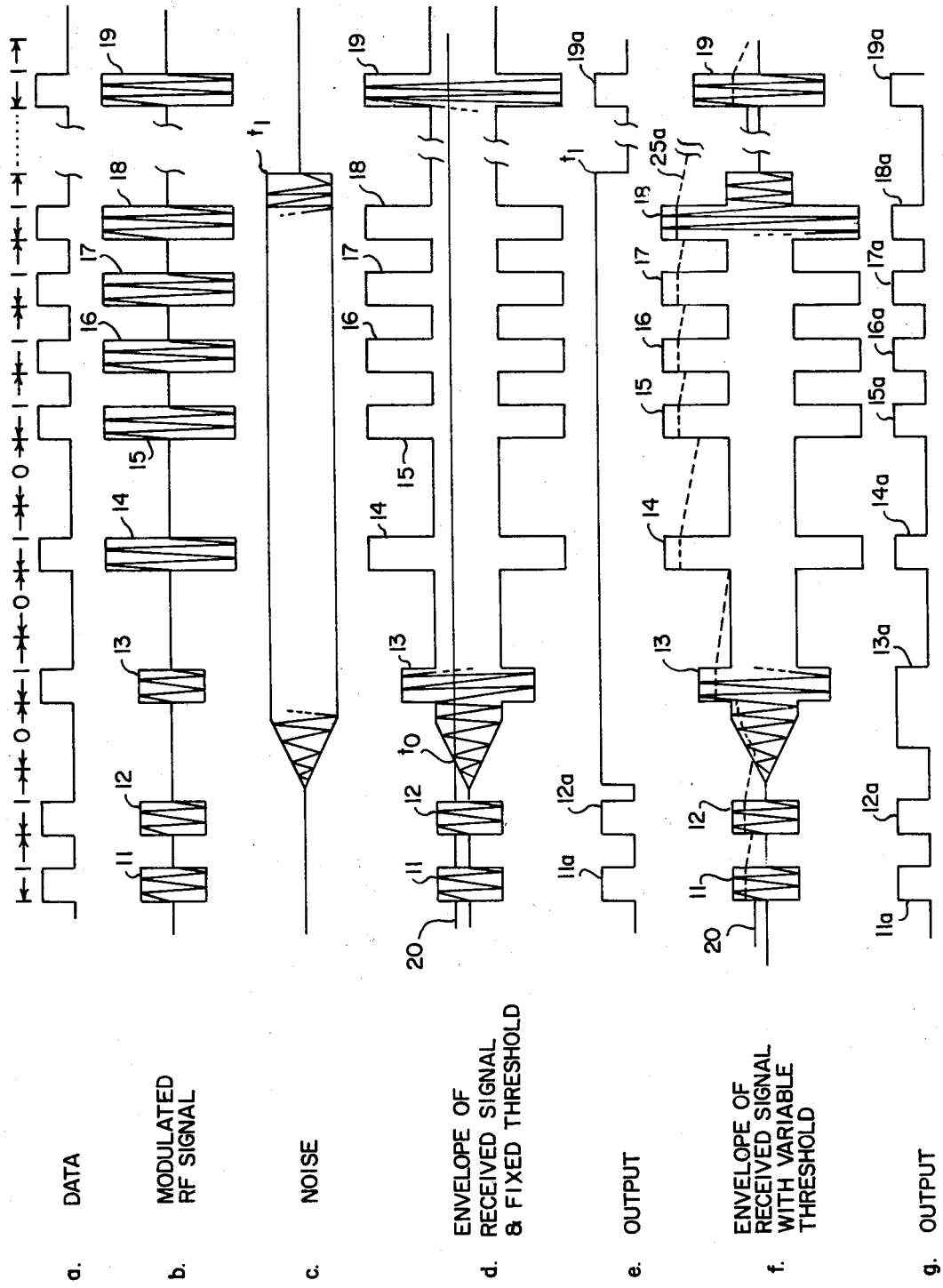
FIG. 1 is a multi-line waveform diagram useful in explaining the disadvantages of the prior art and the advantages of the present invention.

The disadvantages of the prior art and the advantages realized with the present invention may best be understood by the following description in connection with FIG. 1.

Data to be transmitted is represented as binary data consisting of a stream of 1's and 0's. As shown in line a, each "1" is assumed to have a high level during the first half of each bit period. A "0" is represented by a low level during the entire bit period. In line b an RF signal, modulated by the binary data, is diagrammed. For explanatory purposes, the first three 1's are represented by signals 11–13 of a first amplitude while the next six 1's are represented by signals 14–19 of a larger amplitude. Line c is used to diagram an envelope of noise. The envelope of the signal which includes the noise and which is assumed to be received by an AM receiver is diagrammed in line d.

In a conventional AM receiver, a fixed low threshold level, designated in line d by 20, is employed in order to maximize sensitivity. In such a receiver if the input signal level is below the threshold 20, the output (see line e) is low. On the other hand if the input signal level is above the threshold the output is high. For the particular diagrammed arrangement, noiseless signals 11 and 12 have amplitudes above the threshold 20. Thus, they produce high outputs (line e) which represent the first two 1's. Then at time $t_o$ when the noise level equals the threshold 20, the output goes high. It remains high as long as the noise is not less than the threshold 20. Thus any 1's in the received signal do not affect the output. This is true regardless of the amplitudes of the received signals, such as signal 13 which is of one amplitude, and the larger amplitude signals 14–18. Only after the termination of the noise at $t_1$ does the output vary as a function of the received signal, such as signal 19.

From the foregoing it should be appreciated that in an AM receiver with a fixed low threshold, the receiver is very sensitive to noise. As long as the amplitude of the noise reaches or exceeds the fixed threshold, any received signals, during the presence of the noise, are obliterated from the output. Thus output data from the receiver is greatly affected by the noise. Such sensitivity to noise is undesirable in any data transmission system. It is particularly intolerable in an arrangement in which signals are transmitted to an implanted device which is designed to monitor and/or perform certain functions in the body, such as to stimulate certain muscles or nerves. In such a case accuracy of the received signals is of great importance to insure safe operation of the implanted device.

To overcome the disadvantages of the prior art, an implantable AM receiver is provided in which the threshold, rather than being fixed, is variable as a function of the peak amplitude of the received signals including the noise. This important aspect of the invention may best be described in connection with FIG. 1 line f, wherein the threshold of the AM receiver of the present invention is designated by 25. Therein the envelope of the received signals, including noise, such as that shown in line d is also diagrammed. In the AM receiver of the present invention the amplitude of the threshold 25 is chosen to be a selected percentage, e.g., 50 percent, of the peak amplitude of the received signal, including noise. If the threshold is less than this selected percentage, circuitry to achieve a very fast rise time is provided so that the threshold will quickly rise to the selected percentage of the received signal. In the absence of a signal, the threshold 25 decays at a predetermined rate or rate profile.

As shown in line f, as a result of the first received signals 11 and 12 the amplitude of threshold 25 rises from a predetermined minimum level 20 to the selected percentage of the received signal 11, decays during the period when no signal is present, and then again rises to the selected percentage of the amplitude of signal 12. During the first portion of the noise period, the output of the receiver, as shown in line g is high since the noise level is higher than the threshold 25.

However, when signal 14 is received, since it is of a higher amplitude than the noise (or the preceding signals 11-13) the threshold 25 rises to the selected percentage level as previously explained. At the end of signal 14 the receiver output drops and the threshold decays at the predetermined rate profile until the next signal is received. In the example being discussed, so long as the noise is less than the predetermined percentage of the signal amplitude, and the threshold decay is chosen so that the threshold will not intersect the noise before the next signal pulse is received, the receiver will provide an output corresponding to the envelope of the modulated RF signal, even in the presence of large amounts of noise. If during an extended period neither signals nor noise are received the threshold 25 will decrease according to the predetermined rate profile as designated in line f by 25a. However when signal 19 is received in the absence of noise, even though the threshold is low, an output is produced by the receiver as shown in line g and designated by 19a.

From the foregoing it can be seen that with the receiver of the present invention signals may be detected, even in the presence of noise. If the receiver is found to be jammed by noise, due to the variable threshold, signals can be detected by transmitting to the receiver signals having higher peak amplitudes. Since the threshold is variable and automatically adjusts itself to a percentage of the peak amplitude of the received signal and/or noise, the signals can be made detectable by simply increasing the peak amplitude of the signals so that the threshold rises above the noise.

Although the invention is not intended to be limited to a specific application, it is particularly advantageous when incorporated in an implantable device to which signals are transmitted to control operations of circuits in the device. In some contemplated implantable systems, the implanted device includes a transmitter which transmits out of the body signals indicative of those detected by the receiver. External to the body these signals are compared with the originally transmitted signals for verification purposes.

In a system having a conventional implanted AM receiver, if noise jams the receiver, nothing can be done to overcome this problem. Increasing the amplitudes of the signals will not help, since the threshold is fixed at a level below the noise. Thus, when a doctor causes signals to be transmitted to the receiver to control the implanted device, if due to noise the signals are jammed, the signals transmitted from the implanted device to the external unit are not identical to those originally transmitted. The doctor has no means to overcome the noise and cause the desired signals to control the device. However, with the novel AM receiver of the present invention, if the signals received from the implanted device are not the same as those originally transmitted, the doctor may assume that this is due to noise which is greater than the threshold. The presence of the noise may be overcome by merely increasing the peak amplitude of the signals transmitted to the implanted receiver until they are properly detected. This would occur when the signals' peak amplitude is such that the threshold exceeds the noise peak amplitude.

Figure 2:
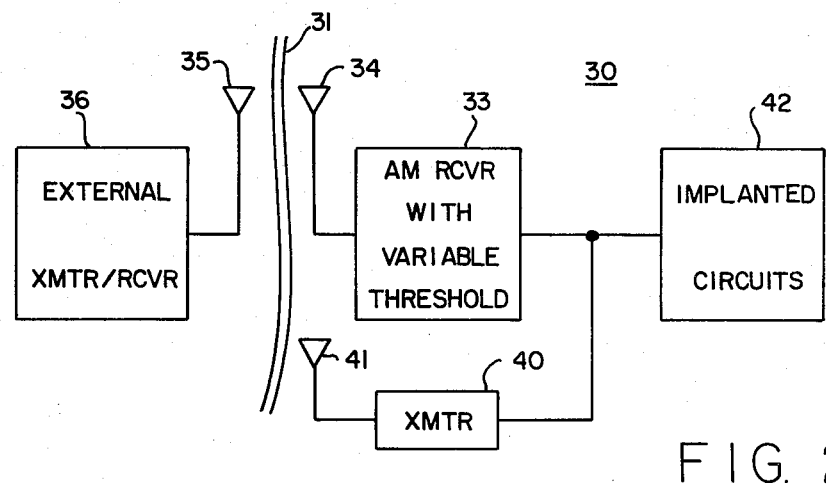
FIG. 2 is a block diagram of an implantable device using a receiver according to the present invention.

Such an arrangement is shown in FIG. 2, wherein the implanted device 30 is shown to the right of 31, which designates a patient's skin. The implanted device 30 is shown to include the novel AM receiver with the variable threshold, designated by 33. By means of antenna 34, it receives signals transmitted from an external antenna 35 of an external transmitter/receiver 36. The latter is assumed to be under the control of an operator, e.g. a doctor, who can control the peak amplitude of the transmitted signals.

The implanted device 30 is also shown to include a transmitter 40 which by means of its antenna 41, transmits to the external transmitter/receiver 36 the output signals of receiver 33. The signals from the latter are also shown being supplied to implanted circuits 42 to control the operations of the latter. This aspect does not form part of the present invention.

With the present invention, if the output signals from the AM receiver 33 to the transmitter 40 for transmission to the external transmitter/receiver 36 differ from those originally transmitted therefrom to the AM receiver 33, the doctor knows that the implanted circuits 42 did not receive the desired signals. If this inconsistency is due to noise jamming the receiver 33, it is easily curable by increasing the peak amplitudes of the signals from the transmitter/receiver 36 to overcome the noise as previously explained. When the signals received from the AM receiver 33 match the signals transmitted by the external transmitter/receiver 36, the doctor knows that the proper signals were received by the implanted circuits 42.

Figure 3:
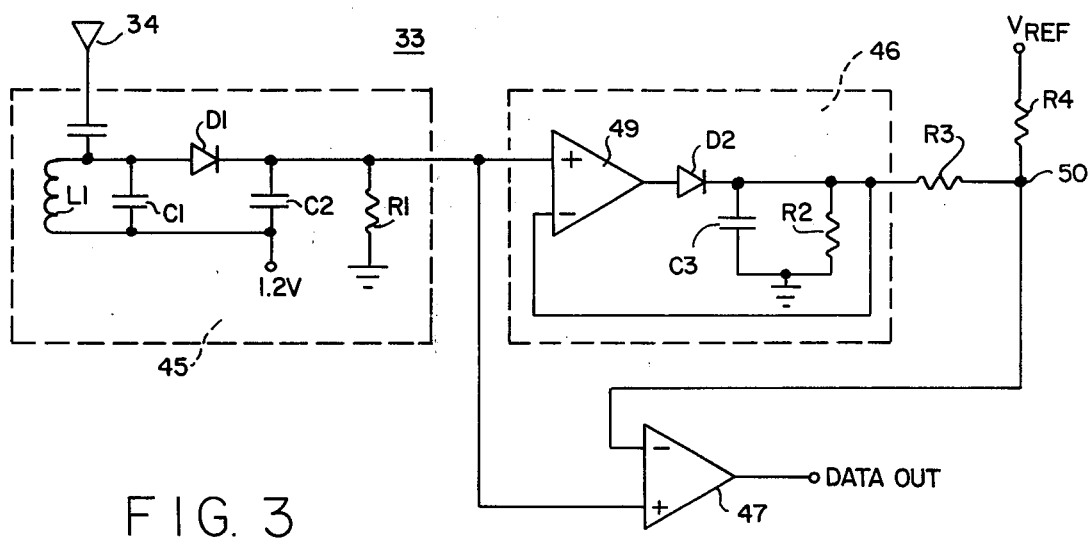
FIG. 3 is a schematic diagram of a receiver according to the present invention.

Attention is now directed to FIG. 3 wherein one embodiment of the AM receiver 33 having the variable threshold is diagrammed. Basically the AM receiver 33 includes a crystal set type AM detector 45 which receives the modulated signals from the antenna 34. It includes an inductor or coil L1 and a capacitor C1, which together form a resonant circuit for the RF Diode D1, the diode D1 being biased slightly by resistor R1 to increase detection sensitivity. Capacitor C2 filters out the RF. The output from the AM detector 45 is supplied to a peak detector 46 and to the positive input of a comparator 47.

The peak detector 46 includes an amplifier 49 which through diode D2 charges up a capacitor C3 which is connected in parallel with a discharge resistor R2, the decay time associated with the C3/R2 combination being chosen to be long with respect to the time between modulated input pulses. It should be recognized that although a single resistor R2 is chosen to establish a predetermined decay rate, a plurality of resistors could be utilized, each of which is connected across the capacitor C3 at predetermined times, thereby establishing any desired decay rate profile. Capacitor C3 charges up to the peak amplitude of the detected signal. The voltage on capacitor C3 is also applied to a resistor R3 which is connected in series with a resistor R4 to a reference potential $V_{REF}$. Resistor R3 and R4 and $V_{REF}$ are chosen so that at junction point 50 the voltage is never greater than the predetermined percentage of the peak amplitude of the voltage on C3 and never less than the predetermined minimum level 20. The voltage at junction 50 is the threshold. This voltage is applied to the negative input of a comparator 47. Thus the output of the comparator 47, which represents the output of an AM receiver 33 (see line g FIG. 1) is low when the signal at the positive input, i.e., the detected signal, is less than the threshold. On the other hand when the peak amplitude is greater than the variable threshold the output of the comparator 47 is high.

Although a capacitor has been chosen as a means to establish the threshold, other means could be utilized. For example, an analog-to-digital converter could be used to convert the output of the AM detector 45 to a digital signal. The digital signal could then be altered in accordance with a predetermined decay rate profile, and then processed by a digital-to-analog converter, thereby providing an analog threshold signal the same as that described in the above embodiment.

Although particular embodiments of the invention have been described and illustrated herein, it is recognized that modifications and variations may readily occur to those skilled in the art and consequently, it is intended that the claims be interpreted to cover such modifications and equivalents.

We claim:

1. An implantable AM receiver for processing amplitude modulated RF signals radiated by an external source, comprising:
   detection means for providing a modulation envelope of received RF signals comprising said radiated amplitude modulated RF signals;
   generation means for developing a variable threshold signal having a value substantially equal to a predetermined percentage of said modulation envelope if said threshold signal is lower than said modulation envelope and a value decreasing in accordance with a predetermined decay profile if said threshold signal is higher than said modulation envelope but not less than a predetermined minimum level; and
   output means for providing an output signal having a first voltage state when said modulation level is greater than said threshold signal and a second voltage state when said modulation envelope is less than said threshold signal.

2. The AM receiver of claim 1 in which said amplitude modulated RF signals comprise pulse modulated RF signals, said generation means comprising:
   a voltage storing and altering means having as an output a voltage level corresponding to that of said modulation envelope whenever said output is below that corresponding to said modulation envelope, and an output that is decreasing according to said predetermined decay profile when said output is above that corresponding to said modulation level; and
   means for obtaining a voltage having a value corresponding to said predetermined percentage of said storing and altering means output voltage but no less than said predetermined minimum level, said voltage comprising said threshold voltage.

3. The AM receiver of claim 1 in which said amplitude modulated RF signals comprise pulse modulated RF signals, said generation means comprising:
   a capacitor;
   first means for charging said capacitor to a voltage level corresponding to that of said modulation envelope whenever said capacitor voltage is below that corresponding to said modulation envelope;
   second means for discharging said capacitor at a rate corresponding to said predetermined decay profile when said capacitor voltage is above that corresponding to said modulation level; and
   third means for obtaining a voltage having a value corresponding to said predetermined percentage of said capactiror voltage but no less than said predetermined minimum level, said voltage comprising said variable threshold signal.

4. The AM receiver of claim 3 in which said generation means first means comprises:
   a parallel LC circuit chosen to be in resonance at said RF signal frequency; and
   a diode in series with said LC circuit and said capacitor thereby charging said capacitor.

5. The AM receiver of claim 3 in which said generation means second means comprises a discharge resistor connected across said capacitor chosen to have a value so that said capacitor will discharge in accordance with said predetermined decay profile.

6. The AM receiver of claim 3 in which said generation means third means comprises:
   a first resistor connected at one end to said capacitor; and
   a second resistor connected at one end to said first resistor other end and at the other end to a reference potential, said first and second resistors being chosen so that a voltage at their interconnection point will be said predetermined percentage of said capacitor voltage, said reference potential being proportional to said predetermined minimum level.

7. The AM receiver of claim 1 in which said output means comprises a comparator.

8. In an implantable AM receiver for receiving pulse modulated RF signals radiated thereto from an external source, said receiver having detection means for providing a modulation envelope corresponding to said received pule modulation RF signal and any noise superimposed thereon, and output means for providing a signal related to a modulation envelope related to said received pulse modulation envelope without any noise superimposed thereon, an improved threshold generation means for controlling said output means comprising:

a capacitor;

means for connecting said capacitor to said detection means whereby a voltage across said capacitor will correspond to said modulation envelope voltage if said modulation envelope voltage is greater than said capacitor voltage;

means for discharging said capacitor at a predetermined decay profile if said modulation envelope voltage is less than said capacitor voltage; and means for providing a threshold voltage corresponding to a voltage having a value equal to a predetermined percentage of said capacitor voltage, but no less than a predetermined minimum voltage whereby said output means will be at a first voltage state whenever said threshold voltage is at a voltage corresponding to a voltage less than that of said modulation envelope and at a second voltage state whenever said threshold voltage is at a voltage corresponding to a voltage greater than that of said modulation envelope.

9. The improved threshold generation means of claim 8 in which said means for discharging comprises:

a discharge resistor; and means for connecting said discharge resistor across said capacitor so that said capacitor will discharge at said predetermined rate.

10. The improved threshold generation means of claim 8 in which said means for providing a threshold voltage comprises:

a reference voltage source having a value related to said predetermined minimum voltage;

a first resistor;

a second resistor chosen to have a value with respect to said first resistor which is related to said predetermined percentage; and means for connecting said first and second resistor combination between said capacitor and said reference voltage source whereby the voltage at said first and second resistor interconnection comprises said threshold voltage.

11. An improved method for receiving a pulse amplitude modulated RF signal by an implanted AM receiver, the steps comprising:

providing a modulation envelope corresponding to the amplitude of the received RF signal;

generally a variable threshold signal having a value substantially equal to a predetermined percentage of said modulation envelope if said threshold signal is lower than said modulation envelope and a value decreasing in accordance with a predetermined decay profile if said threshold signal is higher than said modulation envelope but not less than a predetermined minimum level; and forming an output signal having a first voltage state when said threshold signal is less than said modulations envelope and a second voltage state when said threshold signal is greater than said modulation envelope.

* * * * *